United States Patent [19]

Carr et al.

[11] 3,965,257

[45] June 22, 1976

[54] COMPOSITIONS AND METHODS FOR THE TREATMENT OF THE SYMPTOMS OF HISTAMINE INDUCED ALLERGIC REACTIONS

[75] Inventors: Albert A. Carr; C. Richard Kinsolving, both of Cincinnati, Ohio

[73] Assignee: Richardson-Merrell Inc., Wilton, Conn.

[22] Filed: Jan. 28, 1974

[21] Appl. No.: 437,161

Related U.S. Application Data

[62] Division of Ser. No. 221,823, Jan. 28, 1972, Pat. No. 3,806,526.

[52] U.S. Cl. ............................... 424/45; 424/248; 424/251; 424/267
[51] Int. Cl.² ............................................ A61K 31/535
[58] Field of Search ............... 424/45, 248, 251, 267

[56] References Cited
UNITED STATES PATENTS

| | | | |
|---|---|---|---|
| 2,739,968 | 3/1956 | Sperber et al. | 260/293.8 |
| 3,068,237 | 12/1962 | Rorig | 260/293.84 |
| 3,080,372 | 3/1963 | Janssen | 260/293.68 |
| 3,097,209 | 7/1963 | Janssen | 260/293.68 |
| 3,122,555 | 2/1964 | Janssen | 260/293.68 |

OTHER PUBLICATIONS

Stedman's Medical Dictionary, 21st Edition, (1969), p. 52.

*Primary Examiner*—Norman A. Drezin
*Attorney, Agent, or Firm*—L. Ruth Hattan; Eugene O. Retter; George W. Rauchfuss, Jr.

[57] ABSTRACT

Novel compounds useful as antihistamine agents, antiallergy agents, and bronchodilators are represented by the following formula

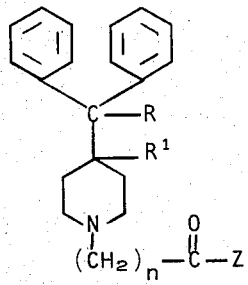

wherein R represents hydrogen or hydroxy; $R^1$ represents hydrogen; or R and $R^1$ taken together form a second bond between the carbon atoms bearing R and $R^1$; n is a positive whole integer of from 1 to 3; Z represents thienyl, phenyl, or substituted phenyl wherein the substituents on the substituted phenyl may be attached at the ortho, meta, or para positions of the phenyl ring and are selected from halogen, a straight or branched lower alkyl chain of from 1 to 4 carbon atoms, a lower alkoxy group of from 1 to 4 carbon atoms, di(lower)alkylamino, or a saturated monocyclic heterocyclic group such as pyrrolidino, piperidino, morpholino, or N-(lower)alkylpiperazino. Pharmaceutically acceptable acid addition salts and individual optical isomers of compounds of the above formula are also included as a part of this invention.

27 Claims, No Drawings

COMPOSITIONS AND METHODS FOR THE TREATMENT OF THE SYMPTOMS OF HISTAMINE INDUCED ALLERGIC REACTIONS

RELATIONSHIP TO OTHER APPLICATIONS

This application is a divisional of application Ser. No. 221,823 filed Jan. 28, 1972 now U.S. Pat. 3,806,526, issued Apr. 23, 1974.

FIELD OF INVENTION

This invention relates to novel substituted piperidine derivatives. More particularly this invention relates to 4-diphenylmethyl-, 4-($\alpha$-hydroxy-$\alpha$-phenylbenzyl)-, and 4-diphenylmethylenepiperidine derivatives which are useful as antihistamines, antiallergy agents and bronchodilators and to methods of making and using the same.

SUMMARY OF INVENTION

The novel substituted piperidine derivatives of this invention useful as antihistamines, antiallergy agents, and bronchodilators are presented by the formula

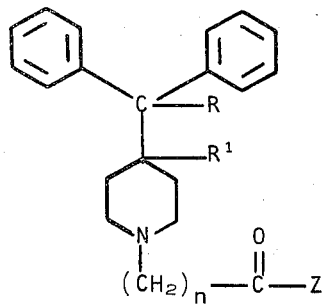

Formula I wherein R represents hydrogen or hydroxy; $R^1$ represents hydrogen; or R and $R^1$ taken together form a second bond between the carbon atoms bearing R and $R^1$; n is a positive whole integer of from 1 to 3; Z represents thienyl, phenyl or substituted phenyl wherein the substituents on the substituted phenyl are selected from an halogen atom, such as chlorine, fluorine, bromine, or iodine, a straight or branched lower alkyl chain of from 1 to 4 carbon atoms, a lower alkoxy group of from 1 to 4 carbon atoms, a di(lower)alkylamino group, or a saturated monocyclic heterocyclic group such as pyrrolidino, piperidino, morpholino, or N-(lower)alkylpiperazino and may be attached at the ortho, meta, or para positions of the phenyl ring. Included in the scope of this invention are the pharamaceutically acceptable acid addition salts and individual optical isomers of the compounds of Formula I.

DETAILED DESCRIPTION OF INVENTION

It can be seen from the above Formula 1 that compounds of this invention may be 4-diphenylmethylpiperidine derivatives as represented by the following Formula II, 4-($\alpha$-hydroxy-$\alpha$-phenylbenzyl)piperidine derivatives as represented by the following Formula III, or 4-diphenylmethylenepiperidine derivatives as represented by the following Formula IV.

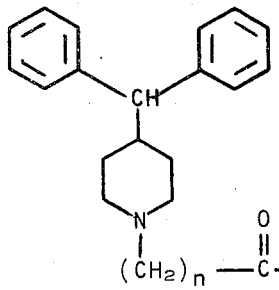

Formula II

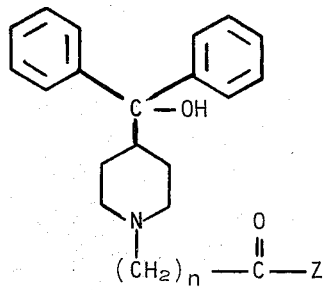

Formula III

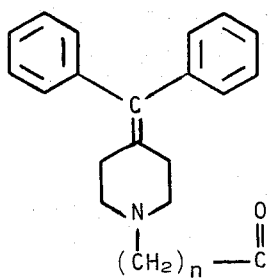

Formula IV

In the above Formulas II, III and IV, n and Z have the same meanings defined hereinbefore.

The term lower alkyl as used in describing the compounds of this invention is taken to mean a straight or branched alkyl chain of from 1 to 4 carbon atoms. As examples of lower alkyl groups that may be present in the compounds of Formulas I to IV as a straight or branched lower alkyl substituent, or in the di(lower)alkylamine substituent, or in the N-(lower)alkylpiperazine substituent on Z when Z represents a substited phenyl there may be mentioned, methyl, ethyl, n-propyl, n-butyl, isopropyl, isobutyl and tert-butyl.

The preferred compounds of this invention are those of general Formulas II and III wherein n and Z have the meanings defined hereinbefore. These compounds have superior antihistamine and antiallergy properties and are bronchodilators. In addition these compounds are characterized by minimal central nervous system stimulant and depressant effects, thus making them particularly useful as antihistamines, antiallergy agents, and bronchodilators.

The more preferred compounds of this invention are those of general Formula III wherein n is equal to 3, and Z has the meaning defined hereinbefore and are represented by the following general Formula V.

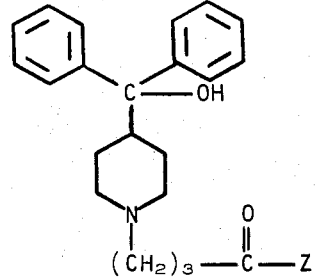

Formula V

In the above general Formula V, Z has the meaning defined hereinbefore.

This invention also includes the pharmaceutically acceptable acid addition salts of the compounds of the hereinbefore set forth formulas, optical isomers and salts thereof. Pharmaceutically acceptable acid addition salts of the compounds of this invention are those of any suitable inorganic or organic acid. Suitable inorganic acids are, for example, hydrochloric, hydrobromic, sulphuric, phosphoric acids and the like. Suitable organic acids include carboxylic acids such as, for example, acetic, propionic, glycolic, lactic, pyruvic, malonic, succinic, fumaric, malic, tartaric, citric, ascorbic, maleic, hydroxymaleic, and dihydroxymaleic, benzoic, phenylacetic, 4-aminobenzoic, 4-hydoxybenzoic, anthranilic, cinnamic, salicylic, 4-aminosalicyclic, 2-phenoxybenzoic, 2-acetoxybenzoic, mandelic acid and the like, sulfonic acids such as, for example, methanesulfonic, ethanesulfonic, $\beta$-hydroxyethanesulfonic acid, and the like.

As examples of compounds illustrative of this invention there may be mentioned, for example, 4'-fluoro-4-(4-diphenylmethylenepiperidino)butyrophenone, 3-(4-diphenylmethylenepiperidino)-1-(2-thienyl)-1-propanone, 4-(4-diphenylmethylenepiperidino)butyrophenone, 4'-ethyl-4-(4-diphenylmethylpiperidino)-butyrophenone, 4'-fluoro-4-[4-($\alpha$-hydroxy-$\alpha$-phenylbenzyl)piperidino]butyrophenone, 4'-fluoro-3-[4-($\alpha$-hydroxy-$\alpha$-phenylbenzyl)piperidino]propiophenone, 4-[4-($\alpha$-hydroxy-$\alpha$-phenylbenzyl)piperidino]-4'-piperidinobutyrophenone, 2-(4-diphenylmethylpiperidino)acetophenone, 4'-ethyl-3-[4-($\alpha$-hydroxy-$\alpha$-phenylbenzyl)piperidino]propiophenone, 4'-di-n-propylamino-4-[4-($\alpha$-hydroxy-$\alpha$-phenylbenzyl)-piperidino]butyrophenone, 4'-tertbutyl-4-[4-($\alpha$-hydroxy-$\alpha$-phenylbenzyl)piperidino]butyrophenone, and the like.

As examples of the more preferred compounds of this invention there may be mentioned, for example, 4'-ethyl-4-[4-($\alpha$-hydroxy-$\alpha$-phenylbenzyl)piperidino]-butyrophenone, 4-[4-($\alpha$-hydroxy-$\alpha$-phenylbenzyl)-piperidino]-4'-piperidinobutyrophenone, 4-[4-($\alpha$-hydroxy-$\alpha$-phenylbenzyl)piperidino]-4'-dimethylaminobutyrophenone, 4-[4-($\alpha$-hydroxy-$\alpha$-phenylbenzyl)piperidino]butyrophenone, 4-[4-($\alpha$-hydroxy-$\alpha$-phenylbenzyl)piperidino]-4'-methoxybutyrophenone, 4'-tert-butyl-4-[4-($\alpha$-hydroxy-$\alpha$-phenylbenzyl)-piperidino]butyrophenone, 4[4-($\alpha$-hydroxy-$\alpha$-phenylbenzyl)piperidino]-1-(2-thienyl)-1-butanone, 4'-fluoro-4-[4-($\alpha$-hydroxy-$\alpha$-phenylbenzyl)-piperidino]-butyrophenone, and the like.

The novel compounds of this invention are useful as antihistamines, antiallergy agents and bronchodilators and may be administered alone or with suitable pharmaceutical carriers, and can be in solid or liquid form such as, for example, tablets, capsules, powders, solutions, suspensions, or emulsions.

The compounds of this invention can be administered orally, parenterally, for example, subcutaneously, intravenously, intramuscularly, intraperitoneally, by intranasal instillation or by application to mucous membranes such as that of the nose, throat, and bronchial tubes, for example, in an aerosol spray containing small particles of a compound of this invention in a spray or dry powder form.

The quantity of novel compounds administered will vary. Depending on the patient and the mode of administration, the quantity of novel compound administered may vary over a wide range to provide in a unit dosage of from about 0.01 to 20 milligrams per kilogram of body weight of the patient per dose to achieve the desired effect. For example the desired antihistamine, antiallergy and bronchodilator effects can be obtained by consumption of a unit dosage form such as, for example, a tablet containing 1 to 50 milligrams of a novel compound of this invention taken 1 to 4 times daily.

The solid unit dosage forms can be of the conventional type. Thus, the solid form can be a capsule which can be of the ordinary gelatin type containing a novel compound of this invention and a carrier, for example, lubricant and inert fillers such as lactose, sucrose, corn starch, and the like. In another embodiment, the novel compounds are tabletted with conventional tablet bases such as lactose, sucrose, corn starch, and the like in combination with binders such as acacia, corn starch or gelatin, disintegrating agents such as corn starch, potato starch, or alginic acid, and a lubricant such as stearic acid, or magnesium stearate.

The novel compounds may also be administered as injectable dosages by solution or suspension of the compounds in a physiologically acceptable diluent with a pharmaceutical carrier which can be a sterile liquid such as water and oils, with or without the addition of a surfactant and other pharmaceutically acceptable adjuvants. Illustrative of oils there can be mentioned those of petroleum, animal, vegetable or synthetic origin, or example, peanut oil, soybean oil, mineral oil, and the like. In general, water, saline, aqueous dextrose, and related sugar solutions, ethanols and glycols such as propylene glycol or polyethylene glycol are preferred liquid carriers, particularly for injectable solutions.

For use as aerosols the novel compounds in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen, propane, etc. with the usual adjuvants such as co-solvents, and wetting agents, as may be necessary or desirable. The compounds may also be administered in a non-pressurized form such as in a nebulizer or atomizer.

To illustrate the utility of the compounds of this invention the following tabulation indicates the amount of certain representative compounds of this invention required to reduce by 50% wheals induced by intradermal injections of 1y of histamine into guinea pigs. Each compound was orally administered one hour prior to the histamine injection.

| Ex. no. | Compound | $ED_{50}$ mg/kg |
| --- | --- | --- |
| 4 | 4-[4-($\alpha$-Hydroxy-$\alpha$-phenylbenzyl)-piperidino]-1-(2-thienyl)butan-1-one hydrochloride | 3.1 |
| 5 | 4-[4-($\alpha$-Hydroxy-$\alpha$-phenylbenzyl)-piperidino]-4'-methylbutyrophenone hydrochloride | 1.9 |
| 6 | 4'-tert-Butyl-4-[4-($\alpha$-hydroxy-$\alpha$-phenylbenzyl)piperidino]butyrophenone hydrochloride | 1.8 |
| 9 | 4-[4-($\alpha$-Hydroxy-$\alpha$-phenylbenzyl)-piperidino)-4'-piperidinobutyrophenone | 3.4 |

The minimal amounts of the compounds of Examples 4,5,6 and 9 required to prevent aerosol antigen induced bronchial spasms and death in the quinea pig are respectively 1.0, 4.0, 1.0 and 4.0 milligrams per kilogram of body weight orally.

The example numbers of the above mentioned compounds correspond to the example numbers of the specific examples of compounds used to illustrate the invention.

The compounds of this invention may be prepared by several methods. Some of the compounds of this invention are used to prepare other compounds of the invention as will be apparent from the following. The compounds of Formula I may be prepared by reacting a substituted piperidine, compound 1, with an ω-haloalkyl aryl ketone, compound 2, as indicated by the following:

$$\text{1} + \text{halo-(CH}_2)_n\text{-C(=O)-Z} \rightarrow \text{Formula I}$$

In the above reaction halo represents a reactive halogen atom, R, $R^1$, n and Z have the meanings defined in Formula I.

The above reaction is carried out in alcoholic solvents such as methanol, ethanol, isopropyl alcohol, n-butanol, and the like, in ketone solvents such as methyl isobutyl ketone, and the like, in hydrocarbon solvents such as benzene, toluene, and the like, or in halogenated hydrocarbons, such as chlorobenzene, and the like, in the presence of an inorganic base such as sodium bicarbonate, potassium carbonate and the like, or in the presence of an organic base such as triethylamine, or an excess of compound 1. In some cases it may be desirable to add catalytic amounts of potassium iodide to the reaction mixture. The reaction time is usually about 48 hours, but may vary from about 4 to 120 hours at a temperature of from about 70°C to the reflux temperature of the solvent.

The ω-haloalkyl aryl ketone derivatives, compound 2, are commercially available, or may be prepared by reacting the appropriate ω-haloalkanoyl halide and aromatic compounds in the presence of aluminum chloride. They may also be prepared by reacting a substituted phenyl Grignard reagent with ω-haloalkanonitriles, followed by the usual work up.

The 4-diphenylmethylpiperidine and α,α-diphenyl-4-piperidinemethanol starting materials as represented by compound 1 wherein R is hydrogen or hydroxy, and $R^1$ is hydrogen are commercially available. 4-Diphenylmethylenepiperidine as represented by compound 1 wherein R and $R^1$ form a second bond between the carbon atoms bearing R and $R^1$ may be prepared by dehydration of α,α-diphenyl-4-piperidinemethanol by generally known procedures.

The compounds of Formula 1 wherein n is the integer 2, may also be prepared by a Mannich Reaction of α,α-diphenyl-4-piperidinemethanol with a methyl aryl ketone derivative of the formula $$CH_3-C(=O)-Z,$$

wherein Z has the meaning defined in Formula 1, in the presence of formaldehyde. Suitable solvents for this reaction include acetic acid, methanol, ethanol, n-propanol, n-butanol and the like. The reaction is carried out in the presence of a small amount of mineral acid, such as, for example, concentrated hydrochloric acid for about 3 to 24 hours, generally about 8 hours, at a temperature of from about 50°–100°C.

The compounds of Formula 1 may also be prepared by the reaction of an appropriately substituted 1-piperidinealkanonitrile with an organometallic compound such as an aryl Grignard or an aryllithium compound in a solvent such as diethyl ether or tetrahydrofuran followed by isolation and purification of the aryl 4-substituted piperidinoalkyl ketone derivative by generally known procedures. The nitrile derivative is obtained by the reaction of an appropriately substituted piperidine compound with an haloalkylnitrile.

The compounds of Formula 1 wherein Z represents a substituted phenyl wherein the substituents on the substituted phenyl are selected from a di(lower)alkylamino group or a saturated monocyclic heterocyclic group and are attached at the ortho- or para- position of the phenyl ring may also be prepared from the corresponding halogen substituted phenyl derivative, preferably a fluoro derivative, using an excess of the dialkylamine or the heterocyclic amine. When volatile amines are employed the amine may be bubbled through a solution of the halogen substituted phenyl derivative in dimethylsulfoxide at about 100°C for about 4 to 8 hours. When higher boiling amines are employed such as, for example, piperidine, excess amounts of the amine are used as base, reactant, and solvent for the reaction which is carried out at the reflux temperature of the amine for about 4 to 24 hours.

The following specific examples are illustrative of the invention.

EXAMPLE 1

4'-Fluoro-4-[4-(α-hydroxy-α-phenylbenzyl)-piperidino]-butyrophenone hydrochloride A mixture of 26.73 g (0.1 mole) of α,α-diphenyl-4-piperidinemethanol, 22 g (0.11 mole) of 4-chloro-4'-fluorobutyrophenone, a trace of potassium iodide and 13.5 g (0.16 mole) of sodium bicarbonate in 500 ml of toluene was refluxed for 2½ days. The mixture was filtered, and the filtrate was cooled. The resulting solid was converted by generally known methods to the hydrochloride salt which was recrystallized from methanol and butanone to give the desired product, M.P. 224.5°–225.5°C.

EXAMPLE 2

4'-Fluoro-3-[4-(α-hydroxy-α-phenylbenzyl)-
piperidino]propiophenone hydrochloride A mixture of 30.4 g (0.1 mole) of α,α-diphenyl-4-piperidinemethanol hydrochloride, 9 g (0.3 mole) of paraformaldehyde and 13.8 g (0.1 mole) of 4'-fluoroacetophenone in 100 ml of isopropyl alcohol containing 2 drops of concentrated HCl was refluxed for 24 hours. The mixture was filtered and the filtrate concentrated to about 100 ml and cooled. The resulting precipitate was filtered off and recrystallized from ethanol and isopropyl alcohol to give the desired product, M.P. 250° C.

EXAMPLE 3

4-[4-(α-Hydroxy-α-phenylbenzyl)piperidino]-
butyrophenone hydrochloride

To 53.4 g (0.2 mole) of α,α-diphenyl-4-piperidinemethanol in 1 liter of toluene was added 38.4 g (0.21 mole) of 4-chlorobutyrophenone, 21 g (0.25 mole) of sodium bicarbonate and 0.1 g of potassium iodide. The mixture was stirred and refluxed for 72 hours then filtered. The filtrate was concentrated to 300 ml and allowed to stand at room temperature until a precipitate formed. The precipitate was filtered off and dissolved in hot toluene, filtered and cooled. A solid formed which was dissolved in diethyl ether and treated with ethereal HCl. The resulting product was recrystallized from methanolbutanone to give the title compound, M.P. 193.5°–195°C.

EXAMPLE 4

4-[4-(α-Hydroxy-α-phenylbenzyl)piperidino]-1-(2-thienyl)-butan-1-one hydrochloride A mixture of 53.5 g (0.2 moles) of α,α-diphenyl-4-piperidinemethanol, 41.5 g (0.22 mole) of 4-chloro-1-(2-thienyl)-1-butanone, 33.6 g (0.4 mole) of sodium bicarbonate and a small amount of potassium iodide in 1 liter of toluene was refluxed for 24 hours then filtered. The filtrate was cooled to room temperature, treated with charcoal, and filtered. The solvent was removed under vacuum and 500 ml of diethyl ether was added to dissolve the residue, followed by treatment with ethereal HCl. The resulting precipitate was recrystallized from methanolbutanone to give the desired product, M.P. 192.5°–193.5°C.

EXAMPLE 5

4-[4-(α-Hydroxy-α-phenylbenzyl)piperidino]-4'-methylbutyrophenone hydrochloride

A mixture of 53.5 g (0.2 moles) of α,α-diphenyl-4-piperidinemethanol 43.3 g (0.22 mole) of 4-chloro-4'-methylbutyrophenone, 33.6 g (0.4 mole) of sodium bicarbonate and a small amount of potassium iodide in 1300 ml of toluene was refluxed for 17 hours collecting the evolved water in a Dean-Stark trap. The mixture was filtered and the solvent removed. The residue was dissolved in ether and treated with ethereal HCl, and the resulting precipitate was washed with dry ether and recrystallized from ethyl acetate-methanol and from isopropyl alcohol to give the desired product, M.P. 236°–237°C.

EXAMPLE 6

4'-tert-Butyl-4-[4-(α-hydroxy-α-phenylbenzyl)-
piperidino]butyrophenone hydrochloride A mixture of 107 g (0.4 mole) of α,α-diphenyl-4-piperidinemethanol, 105 g (0.44 mole) of 4'-tert-butyl-4-chlorobutyrophenone, 70 g (0.7 mole) of potassium bicarbonate, and a small amount of potassium iodide in 600 ml of toluene was refluxed and stirred for 2½ days then filtered. The filtrate was treated with charcoal, filtered through celite then treated with ethereal HCl. The resulting solid was recrystallized from methanol and isopropyl alcohol to give the desired product, M.P. 234°–235°C.

EXAMPLE 7

4'-Bromo-4-[4-(α-hydroxy-α-phenylbenzyl)-
piperidino]-butyrophenone hydrochloride A mixture of 45.4 g (0.17 mole) of α,α-diphenyl-4-piperidinemethanol, 49.99 g (0.19 mole) of 4'-bromo-4-chlorobutyrophenone, 30 g (0.3 mole) of potassium bicarbonate and 700 ml of toluene was refluxed for 3 days. Upon cooling to room temperature the mixture was filtered, and the filtrate was cooled and treated with ethereal HCl then ether. The resulting solid was washed with ether, dried, and dissolved in 2 liters of methanol. The solution was treated with charcoal, filtered, and concentrated to a 500 ml volume. Isopropyl alcohol was added to the concentrate and heated to a vapor temperature of 73°C. The concentrate was cooled to room temperature, and a product crystallized which was washed with isopropyl alcohol then ether and recrystallized from isopropyl alcohol-water, and isopropyl alcohol to give the title compound, M.P. 251°–252.5°C.

EXAMPLE 8

4'-Fluoro-2-[4-(α-hydroxy-α-phenylbenzyl)-
piperidino]-acetophenone hydrochloride hydrate To 40 g (0.15 mole) of α,α-diphenyl-4-piperidinemethanol in 800 ml of benzene was added 16.8 g (0.2 mole) of sodium bicarbonate followed by 27.6 g (0.16 mole) of 2-chloro-4'-fluoroacetophenone in 25 ml of benzene. The mixture was stirred and refluxed for 53 hours, filtered, and the filtrate was concentrated to an oil. The oil was dissolved in diethyl ether, washed with water, dried over anhydrous magnesium sulfate, filtered and treated with ethereal HCl. The resulting precipitate was recrystallized from ethanol-water and ethanol-hexane to give the title compound, M.P. 171°–174°C, (anhydrous 231°–3°C).

EXAMPLE 9

4-[4-(α-Hydroxy-α-phenylbenzyl)piperidino]-4'-
piperidinobutyrophenone

A mixture of 15 g (0.035 mole) of 4'-fluoro-4-[4-(α-hydroxy-α-phenylbenzyl)piperidino]butyrophenone, the free base of the compound of Example 1, and a small amount of potassium iodide in 100 ml of piperidine was refluxed for 22 hours. The unreacted piperidine was removed under vacuum, and the remaining residue was triturated with water, the water decanted, and the residue dissolved in methanol and added to a large amount of water. The resulting precipitate was dissolved in a large volume of ether, dried over magnesium sulfate, treated with charcoal and filtered. The filtrate was concentrated to a 50 ml volume and cooled, yielding a product which was recrystallized from ether to give the title compound, M.P. 137.5°–139°C.

EXAMPLE 10

4-(4-Diphenylmethylpiperidino)butyrophenone hydrochloride

A mixture of 175.5 g (0.7 mole) of 4-diphenylmethylpiperidine, 63.6 g (0.35 mole) of 4-chlorobutyrophenone, 600 ml of toluene, and a small amount of potassium iodide was refluxed for three days then allowed to stand at room temperature one day. The solvent was removed at reduced pressure, and one liter of dry ether was added after which the mixture was filtered. The filtrate was concentrated, and the residue was dissolved in 75°–90° petroleum ether treated with charcoal and filtered. The filtrate was cooled to room temperature and the resulting precipitate was filtered off, and dissolved in ether then treated with ethereal HCl. A precipitate formed which was recrystallized from methanol-butanone to give the desired product, M.P. 163.5°–164.5°C.

EXAMPLE 11

4-(4-Diphenylmethylpiperidino)-4'-fluorobutyrophenone hydrochloride

A mixture of 125.5 g (0.5 mole) of 4-diphenylmethyl-piperidine, 110 g (0.55 mole) of 4'-fluoro-4-chlorobutyrophenone, 110 g (0.8 mole) of potassium carbonate, a small amount of potassium iodide and 600 ml of methyl isobutyl ketone was refluxed and stirred for 2½ days, then filtered. The filtrate was concentrated under reduced pressure. The remaining residue was dissolved in ether and treated with ethereal HCl. A gummy residue formed which was dissolved in ethyl acetate with a small amount of water and heated on a steam bath to a vapor temperature of 77°C then cooled. The resulting precipitate was washed with ether and recrystallized from ethyl acetate, toluene and isopropyl alcohol to give the desired product, M.P. 194°–195.5°C.

EXAMPLE 12

4'-Dimethylamino-4-[4-($\alpha$-hydroxy-$\alpha$-phenylbenzyl)-piperidino]butyrophenone Through a solution of 18 g (0.041 mole) of 4'-fluoro-4-[4-($\alpha$-hydroxy-$\alpha$-phenylbenzyl)piperidino]-butyrophenone in 150 ml of dimethylsulfoxide (DMSO) was vigorously bubbled dimethylamine for 6 hours at 100°C. Most of the DMSO was removed at reduced pressure and a temperature of 120°C. The remaining mixture was poured into water and sodium carbonate to which was added a small amount of methanol. The resulting solid was filtered and dissolved in warm methanol and isopropyl alcohol, treated with charcoal filtered, and cooled. The solid which formed upon cooling was filtered off and recrystallized from acetone-heptane to give the desired product, M.P. 148°–150°C.

EXAMPLE 13

By the procedure of Example 11 only substituting for 4'-fluoro-4-chlorobutyrophenone an appropriate amount of 4-chloro-4'-ethylbutyrophenone or 4-chloro-4'-ethoxybutyrophenone the following compounds are obtained:

4-(4-diphenylmethylpiperidino)-4'-ethylbutyrophenone hydrochloride,
4-(4-diphenylmethylpiperidino)-4'-ethoxybutyrophenone hydrochloride.

EXAMPLE 14

By the procedure of Example 9, only substituting for piperidine an appropriate amount of morpholine, N-methylpiperazine or pyrrolidine the following compounds are obtained:

4-[4-($\alpha$-hydroxy-$\alpha$-phenylbenzyl)piperidino]-4'-morpholinobutyrophenone,
4-[4-($\alpha$-hydroxy-$\alpha$-phenylbenzyl)piperidino]-4'-(N-methylpiperazino)butyrophenone.
4-[4-($\alpha$-hydroxy-$\alpha$-phenylbenzyl)piperidino]-4'-pyrrolidinobutyrophenone.

EXAMPLE 15

4'-Fluoro-4-(4-diphenylmethylenepiperidino)-butyrophenone

A mixture of 99.9 g (0.4 mole) of 4-diphenylmethylenepiperidine, 88 g (0.44 mole) of 4-chloro-4'-fluorobutyrophenone, 64.0 g (0.64 mole) of potassium bicarbonate and a small amount of potassium iodide in 1500 ml of toluene was refluxed for 5 days. The reaction mixture was filtered, and the filtrate was concentrated at reduced pressure leaving a residue which was dissolved in about 800 ml of ethyl acetate. This solution was concentrated to about 500 ml and allowed to stand for one day. The resulting precipitate was recrystallized from methanolethyl acetate, made basic with sodium hydroxide solution, water washed, and the product recrystallized from 75°–90° petroleum ether to give the title compound, M.P. 111°–114°C.

EXAMPLE 16

An illustrative composition for hard gelatin capsules is as follows:

| | | |
|---|---|---|
| (a) | 4'-tert-butyl-4-[4-($\alpha$-hydroxy-$\alpha$-phenylbenzyl)piperidino]butyrophenone hydrochloride | 10 mg |
| (b) | talc | 5 mg |
| (c) | lactose | 100 mg |

The formulation is prepared by passing the dry powders of (a) and (b) through a fine mesh screen and mixing them well. The powder is then filled into hard gelatin capsules at a net fill of 115 mg per capsule.

EXAMPLE 17

An illustrative composition for tablet is as follows:

| | | |
|---|---|---|
| (a) | 4'-fluoro-4-[4-($\alpha$-hydroxy-$\alpha$-phenylbenzyl)piperidino]butyrophenone hydrochloride | 5 mg |
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 18

An illustrative composition for an aerosol solution is the following:

|   |   | Weight per cent |
|---|---|---|
| (a) | 4-[4-(α-hydroxy-α-phenylbenzyl)-piperidino]-4'-methylbutyrophenone | 5.0 |
| (b) | ethanol | 35.0 |
| (c) | dichlorodifluoromethane | 60.0 |

The materials (a), (b) and (c) are packaged in 15 ml stainless steel containers equipped with a metering valve designed to meter 0.2 grams per dose, an equivalent of 10 mg of novel compound (a).

EXAMPLE 19

An illustrative composition for an aerosol suspension is the following:

|   |   | Weight per cent |
|---|---|---|
| (a) | 4-[4-(α-hydroxy-α-phenylbenzyl)-piperidino]butyrophenone (particle size <10μ) | 20.0 |
| (b) | sorbitan trioleate | 0.5 |
| (c) | dichlorodifluoromethane | 39.75 |
| (d) | dichlorodifluoroethane | 39.75 |

The materials (a) – (d) are packaged in 15 ml stainless steel containers equipped with a metering valve designed to meter 50 mg per does, an equivalent of 10 mg of novel compound (a).

EXAMPLE 20

An illustrative composition for an injectable suspension is the following 1 ml ampul for an intramuscular injection.

|   |   | Weight per cent |
|---|---|---|
| (a) | 4-[4-(α-hydroxy-α-phenylbenzyl)-piperidino]-4'-methoxybutyrophenone hydrochloride (particle size <10μ) | 1.0 |
| (b) | polyvinylpyrrolidone (M.W. 25000) | 0.5 |
| (c) | lecithin | 0.25 |
| (d) | water for injection to make | 100.0 |

The materials (a) – (d) are mixed, homogenized, and filled into 1 ml ampuls which are sealed and autoclaved 20 minutes at 121°C. Each ampul contains 10 mg per ml of novel compound (a).

EXAMPLE 21

4'-Dimethylamino-2-(4-diphenylmethyl-piperidino)acetophenone mono-hydrochloride

Through a solution of 20g (0.0515 mole) 2-(4-diphenylmethylpiperidino)-4'-fluoroacetophenone in 100 ml of dimethylsulfoxide (DMSO) was bubbled dimethylamine for 6 hours at 100°C. Most of the DMSO was evaporated at reduced pressure, and the remaining mixture was added to water and sodium bicarbonate. The precipitate was removed and converted to the acid hydrochloride which recrystallized from ethyl acetate or butanol or ethanol-ethyl acetate to give the title compound, M.P. 242°–5°C. (Free base of title compound, M.P. 107°–110°C.)

EXAMPLE 22

4'-Ethyl-4-[4-(α-hydroxy-α-phenylbenzyl)piperidino]-butyrophenone hydrochloride

By the procedure of Example 6 only substituting for 4'-tert-butyl-4-chlorobutyrophenone, an appropriate amount of 4'-ethyl-4-chlorobutyrophenone, the desired product is obtained.

EXAMPLE 23

4-[4-(α-Hydroxy-α-phenylbenzyl)piperidino]-4'-methoxybutyrophenone hydrochloride By the procedure of Example 6, only substituting for 4'-tert-butyl-4-chlorobutyrophenone an appropriate amount of 4'- methoxy-4-chlorobutyrophenone, and refluxing the mixture for 48 hours the desired product was obtained upon recrystallization from methanol-butanone, M.P. 219°–221°C.

We claim:

1. A pharmaceutical composition in unit dosage form containing from about 1 to 5 milligrams of a compound of the formula

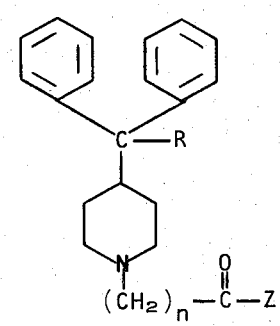

wherein R is selected from the group consisting of hydrogen and hydroxy; n is a positive integer of from 1 to 3; and Z is selected from the group consisting of thienyl, phenyl, and substituted phenyl wherein the substituents on the substituted phenyl may be attached at the ortho, meta, or para positions of the substituted phenyl ring and are selected from the group consisting of a halogen atom, a straight or branched alkyl chain of from 1 to 4 carbon atoms, a lower alkoxy group of from 1 to 4 carbon atoms, a di(lower)alkylamino group, and a saturated monocyclic heterocyclic ring selected from the group consisting of pyrrolidino, piperidino, morpholino, and N-(lower)alkylpiperazino; and a pharmaceutically acceptable acid addition salt thereof and a significant amount of a pharmaceutically acceptable carrier.

2. A composition of claim 1 wherein R represents hydroxy and n is 3.

3. A composition of claim 2 wherein the compound is 4'-tert-butyl-4-[4-(α-hydrozy-α-phenylbenzyl)-piperidino]butyrophenone or a pharmaceutically acceptable acid addition salt thereof.

4. A composition of claim 2 wherein the compound is 4-[4-(α-hydroxy-α-phenylbenzyl)piperidino]-4'-methoxybutyrophenone or a pharmaceutically acceptable acid addition salt thereof.

5. A composition of claim 2 wherein the compound is 4-[4-(α-hydroxy-α-phenylbenzyl)piperidino]-1-(2-thienyl)-1-butanone or a pharmaceutically acceptable acid addition salt thereof.

6. A composition of claim 2 wherein the compound is 4-[4-(α-hydroxy-α-phenylbenzyl)piperidino]-4'-piperidinobutyrophenone or a pharmaceutically acceptable acid addition salt thereof.

7. A composition of claim 2 wherein the compound is 4-[4-(α-hydroxy-α-phenylbenzyl)piperidino]- butyrophenone or a pharmaceutically acceptable acid addition salt thereof.

8. A composition of claim 2 wherein the compound is 4'-fluoro-4-[4-(α-hydroxy-α-phenylbenzyl)-piperidino]-butyrophenone or a pharmaceutically acceptable acid addition salt thereof.

9. A composition of claim 2 wherein the compound is 4'-ethyl-4-[4-(α-hydroxy-α-phenylbenzyl)piperidino]-butyrophenone or a pharmaceutically acceptable acid addition salt thereof.

10. A composition of claim 2 wherein the compound is 4-[4-(α-hydroxy-α-phenylbenzyl)piperidino]-4'-methylbutyrophenone hydrochloride or a pharmaceutically acceptable acid addition salt thereof.

11. A composition of claim 1 wherein said composition is in the form of a solid.

12. A composition of claim 1 wherein said composition is in a form suitable for injection.

13. A composition of claim 1 wherein said composition is in the form of an aerosol.

14. A method of treating the symptoms of an allergic reaction due to histamine in a patient comprising administering to said patient from 0.01 to 20 milligrams per kilogram of body weight of the patient a compound of the formula:

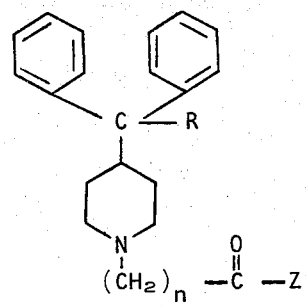

wherein R is selected from the group consisting of hydrogen and hydroxy; n is a positive integer of from 1 to 3; and Z is selected from the group consisting of thienyl, phenyl, and substituted phenyl wherein the substituents on the substituted phenyl amy be attached at the ortho, meta, or para positions of the substituted phenyl ring and are selected from the group consisting of a halogen atom, a straight or branched alkyl chain of from 1 to 4 carbon atoms, a lower alkoxy group of from 1 to 4 carbon atoms, a di(lower) alkylamino group, and a saturated monocyclic heterocyclic ring selected from the group consisting of pyrrolidino, piperidino, morpholino, and N-(lower)alkylpiperazino; and a pharmaceutically acceptable acid addition salt thereof.

15. A method of claim 14 wherein R is hydroxy.

16. A method of claim 15 wherein the compound is 4'-fluoro-2-[4-(α-hydroxy-α-phenylbenzyl)-piperidino]acetophenone or a pharmaceutically acceptable acid addition salt thereof.

17. A method of claim 15 wherein n is equal to 3.

18. A method of claim 17 wherein the compound is 4'-tert-butyl-4-[4-(α-hydroxy-α-phenylbenzyl)-piperidino]butyrophenone or a pharmaceutically acceptable acid addition salt thereof.

19. A method of claim 17 wherein the compound is 4-[4-(α-hydroxy-α-phenylbenzyl)piperidino]-4'-methoxybutyrophenone or a pharmaceutically acceptable acid addition salt thereof.

20. A method of claim 17 wherein the compound is 4-[4-(α-hydroxy-α-phenylbenzyl)piperidino]-1-(2-thienyl)-1-butanone or a pharmaceutically acceptable acid addition salt thereof.

21. A method of claim 17 wherein the compound is 4-[4-(α-hydroxy-α-phenylbenzyl)piperidino]-4'-piperidinobutyrophenone or a pharmaceutically acceptable acid addition salt thereof.

22. A method of claim 17 wherein the compound is 4-[4-(α-hydroxy-α-phenylbenzyl)piperidino]-butyrophenone or a pharmaceutically acceptable acid addition salt thereof.

23. A method of claim 17 wherein the compound is 4'-fluoro-4-[4-(α-hydroxy-α-phenylbenzyl)-piperidino[-butyrophenone or a pharmaceutically acceptable acid addition salt thereof.

24. A method of claim 17 wherein the compound is 4'-ethyl-4-[4-(α-hydroxy-α-phenylbenzyl)piperidino]-butyrophenone or a pharmaceutically acceptable acid addition salt thereof.

25. A method of claim 17 wherein the compound is 4-[4-(α-hydroxy-α-phenylbenzyl)piperidino]-4'-methylbutyrophenone hydrochloride or a pharmaceutically acceptable acid addition salt thereof.

26. A method of inducing bronchial dilation in a patient suffering from bronchial constriction comprising administering to said patient from 0.01 to 20 milligrams per kilogram of body weight of the patient of a compound of the formula

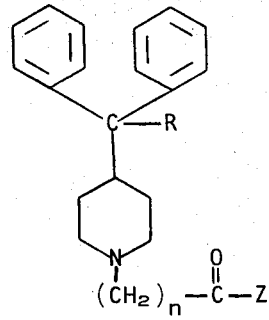

wherein R is selected from the group consisting of hydrogen and hydroxy; n is a positive integer of from 1 to 3; and Z is selected from the group consisting of thienyl, phenyl, and substituted phenyl wherein the substituents on the substituted phenyl may be attached at the ortho, meta, or para positions of the substituted phenyl ring and are selected from the group consisting of a halogen atom, a straight or branched alkyl chain of from 1 to 4 carbon atoms, a lower alkoxy group of from 1 to 4 carbon atoms, a di(lower)alkylamino group, and a saturated monocyclic heterocyclic ring selected from the group consisting of pyrrolidino, piperidino, morpholino, and N-(lower)alkylpiperazino; and a pharmaceutically acceptable acid addition salt thereof.

27. A method of claim 26 wherein R is hydroxy and n is equal to 3.

* * * * *